(12) United States Patent
Chase et al.

(10) Patent No.: US 10,149,828 B2
(45) Date of Patent: Dec. 11, 2018

(54) OXYBUTYNIN TRANSDERMAL THERAPEUTIC SYSTEM COMBINATION

(71) Applicant: CHASE PHARMACEUTICALS CORPORATION, Washington, DC (US)

(72) Inventors: Thomas N. Chase, Washington, DC (US); Kathleen E. Clarence-Smith, Washington, DC (US)

(73) Assignee: Chase Pharmaceuticals Corporation, Madison, NJ (US)

( * ) Notice: Subject to any disclaimer, the term of this patent is extended or adjusted under 35 U.S.C. 154(b) by 0 days.

(21) Appl. No.: 14/991,273

(22) Filed: Jan. 8, 2016

(65) Prior Publication Data

US 2016/0243070 A1 Aug. 25, 2016

Related U.S. Application Data

(60) Provisional application No. 62/101,700, filed on Jan. 9, 2015.

(51) Int. Cl.
| | | |
|---|---|---|
| *A61K 31/222* | (2006.01) | |
| *A61K 31/27* | (2006.01) | |
| *A61K 9/70* | (2006.01) | |
| *A61K 31/216* | (2006.01) | |
| *A61K 31/445* | (2006.01) | |
| *A61K 31/473* | (2006.01) | |
| *A61K 31/4748* | (2006.01) | |
| *A61K 31/55* | (2006.01) | |
| *A61K 45/06* | (2006.01) | |

(52) U.S. Cl.
CPC .......... *A61K 31/222* (2013.01); *A61K 9/7023* (2013.01); *A61K 31/216* (2013.01); *A61K 31/27* (2013.01); *A61K 31/445* (2013.01); *A61K 31/473* (2013.01); *A61K 31/4748* (2013.01); *A61K 31/55* (2013.01); *A61K 45/06* (2013.01)

(58) Field of Classification Search
None
See application file for complete search history.

*Primary Examiner* — Savitha M Rao
*Assistant Examiner* — Gregg Polansky
(74) *Attorney, Agent, or Firm* — Roy Issac

(57) ABSTRACT

There is described a pharmaceutical combination comprising oxybutynin or a pharmaceutically acceptable addition salt thereof, in a transdermal therapeutic system, and an acetylcholinesterase inhibitor, useful for safely treating hypocholinergic disorders of the central nervous system such as Alzheimer type dementia. In this combination, the acetylcholinesterase inhibitor (AChEI) is present at a dose that is higher than the maximal recommended dose, per unit form. In particular, the transdermal therapeutic system comprising oxybutynin is in combination with rivastigmine in a transdermal formulation or oral form.

4 Claims, No Drawings

OXYBUTYNIN TRANSDERMAL THERAPEUTIC SYSTEM COMBINATION

OBJECT OF THE INVENTION

The invention relates to a transdermal therapeutic system containing 4-diethylaminobut-2-ynyl 2-cyclohexyl-2-hydroxy-2-phenylethanoate, known under its International Non-proprietary name as oxybutynin, or a pharmaceutically acceptable salt thereof, in combination with high doses of an acetylcholinesterase inhibitor (AChEI), useful for the treatment of Alzheimer type dementia. The invention also concerns the use of such a combination as a method for enhancing the maximal efficacy and maximal tolerated dose of an AChEI in a patient suffering from dementia of the Alzheimer type.

The invention further relates to a transdermal therapeutic system comprising both oxybutynin and a high dose of (S)-N-Ethyl-N-methyl-3-[1-(dimethylamino)ethyl]-phenyl carbamate, known under its International Non-proprietary name as rivastigmine, or a pharmaceutically acceptable salt thereof. In particular, the transdermal therapeutic system involves delivering a combination of oxybutynin with a high-dose of rivastigmine via transdermal formulation(s) and transdermal patches incorporating such formulations. The present invention also relates to transdermal drug formulations, transdermal patches incorporating such formulations, as well as associated methods of use for treatment of Alzheimer type dementia. The formulations of the present invention can be incorporated into patches for transdermal administration. For instance, a transdermal patch for transdermal delivery of oxybutynin and a transdermal patch for transdermal delivery of an AChEI, preferably, rivastigmine. Alternatively, the transdermal patch for transdermal delivery of oxybutynin is combined with an orally administered AChEI, preferably, rivastigmine.

DEFINITIONS

"Peripheral": refers to anticholinergic agents, and in particular to anticholinergics that are largely unable (have a limited ability) to enter the central nervous system following systemic administration and thus do not affect brain function to a clinically appreciable degree. These drugs can include both quaternary and tertiary ammonium anticholinergic agents, especially those having low lipid solubility.

"Anticholinergic therapy": the treatment with an anticholinergic agent of such medical conditions as gastro-intestinal cramping, nausea, retching, vomiting, fecal incontinence, bladder spasms, urinary incontinence, overactive bladder, asthma, motion sickness, muscular spasms, and smooth muscle contractive disorders; or the treatment with an anticholinergic agent of side effects caused by rivastigmine including, but not limited to gastro-intestinal cramping, nausea, retching, vomiting, fecal incontinence, bladder spasms, urinary incontinence, overactive bladder, asthma, motion sickness, muscular spasms, and smooth muscle contractive disorders.

"CNS": Central Nervous System.
"PNS": Peripheral Nervous System.
"CSF": Cerebrospinal Fluid.
"IR": Immediate Release of the active ingredient from a composition.
"ER": Extended Release (or sustained or controlled release) of the active ingredient from a composition by any administration route.
"AChEI(s)": Acetyl Choline Esterase Inhibitor(s).
"NsPAChA(s)": non-selective, peripheral AntiCholinergic Agent(s).
"Non selective": refers to nsPAChAs, and applies to anticholinergic agents exhibiting inhibitory activity broadly across the various subtypes of muscarinic M-receptors, namely the M1-M5 receptors.
Muscarinic type receptors (mAChRs): Five subtypes of muscarinic receptors, M1 through M5, have been identified.
"Transdermal therapeutic system", or "TTS" is targeted to delivery of drug to skin tissues just under the skin, regional tissues, using transdermal drug formulations and transdermal patches incorporating such transdermal drug formulations.
"Maximum tolerated dose," "maximal tolerated dose" or "MTD" refers to, and is defined as the highest dose of a drug or treatment that does not cause unacceptable side effects. The maximum tolerated dose is determined in clinical trials by testing increasing doses on different groups of people until the highest dose with acceptable side effects is found. The expression "per single dose" refers to a dose of AChEI taken once, independently of the number of the taken dosage units.

BACKGROUND OF THE INVENTION

Reduced levels of neurotransmitters including acetylcholine occur in dementias of the Alzheimer type. In particular, a deficit in acetylcholine-mediated transmission is thought to contribute to the cognitive and neurobehavioral abnormalities associated with these disorders. Accordingly, drugs known to augment cholinergic transmission in the CNS are the mainstay of current therapy.

Acetylcholinesterase inhibitors (AChEIs) are now not only part of the standard of care for patients suffering from a dementia of the Alzheimer type, but are also widely used off-label for various other chronic progressive disorders of cognitive function. AChEIs have the enhancement of acetylcholine-mediated neurotransmission as a general mechanism of action. All act in the human CNS to increase and prolong the availability of acetylcholine by inhibiting its degradatory enzyme acetylcholinesterase (AChE). Four AChEIs have been approved by the U.S. FDA for the treatment of dementias of the Alzheimer type: tacrine, donepezil [Aricept®], rivastigmine [Exelon®] and galantamine [Razadyne®]. Rivastigmine has also been approved for the treatment of Parkinson's disease dementia. AChEIs are available in various formulations including immediate release forms such as tablets, capsules and solutions as well as rapid dissolving and extended release forms for oral administration as well as those for parenteral (e.g. transdermal) administration.

Advantageous AChEIs are those currently used or tested for this indication, and include, but are not limited to, 1,2,3,4-tetrahydro-9-acridinamine (tacrine), and pharmaceutically acceptable salts thereof, in particular the hydrochloride; 9-amino-2,3,5,6,7,8-hexahydro-1H-cyclopenta[b]quinoline (ipidacrine) and pharmaceutically acceptable salts thereof, in particular the hydrochloride hydrate; (.+−.)-2,3-dihydro-5,6-dimethoxy-2-[[1-(phenylmethyl)-4-piperidinyl]methy-1]-1H-inden-1-one (donepezil) and pharmaceutically acceptable salts thereof, in particular the hydrochloride; 3-[2-(1-benzyl-4-piperidyl)ethyl]-5,7,-dihydro-6H-pyrrolo[3,21]-1,2-benzi-soxazol-6-one (icopezil) and pharmaceutically acceptable salts thereof, in particular the maleate, 3-[1-benzylpiperdin-4-yl]-1-(2,3,4,5-tetrahydro-1H-1-benzazepin-8-yl)prop-an-1-one (zanapezil) and pharmaceutically acceptable salts thereof, in particular the fumarate, (S)—N-Ethyl-N-methyl-3-[1-(dimethylamino)ethyl]-phenyl carbamate (rivastigmine) and pharmaceutically acceptable salts thereof, in particular the hydrogen (2R,3R)-tartrate ("rivastigmine tartrate"), 4aS,6R,8aS-3-methoxy-11-methyl-4a,5,9,10,11,12-hexahydroxy-6H-benzofuro[3-a,3,2-e,f]benzazepin-6-ol (galantamine) and pharmaceutically acceptable salts thereof, in particular the hydrobromide; (1R,9S,13E)-1-amino-13-ethylidene-11-methyl-6-azatricyclo[7.3.1.0.sup.2.7-]trideca-2(7),3,10-trien-5-one (huperzine A) and phenserine and its analogs illustrated in U.S. Pat. No. 8,404,701, the contents of which are incorporated herein in their entirety. Other AChEIs include those described in U.S. Pat. No. 6,683,105, which is incorporated herein in its entirety.

As set forth above, tacrine hydrochloride, donepezil hydrochloride, rivastigmine tartrate and galantamine hydrobromide were approved and are used in the treatment of Alzheimer's type dementia, thus being preferred AChEIs. Huperzine A, which is not an approved drug but is an AChEI currently used for treating Alzheimer type dementia, is included among the preferred AChEIs of the present invention. It is a purified plant (Huperzia serrata) extract identified as (1R,9S,13E)-1-amino-13-ethylidene-11-methyl-6-azatricyclo[7.3.1.0$^{2.7}$]trideca-2(7),3,10-trien-5-one and also obtained by total synthesis (WO 2009/120774).

Huperzine A is available in unit forms at a maximum dose/unit form of 0.2 mg and generally administered twice a day (0.4 mg/day).

Tacrine hydrochloride was approved in oral IR-unit forms at the maximal recommended dose level of 40 mg, and administered alone at a maximal recommended oral daily dose level of 160 mg.

Donepezil hydrochloride is an AChEI approved worldwide in 5-mg and 10 IR-unit forms at the maximal recommended oral dose level of 10 mg, and is administered alone at a maximal recommended oral daily dose level of 10 mg. It is also approved, in the U.S.A only, in a 23-mg oral unit form that is orally administered alone once per day, even though the benefit/risk ratio of this formulation, when administered alone, has been questioned because it is not tolerated in most patients.

Galantamine, as hydrobromide, was approved in oral IR-unit forms at the maximal recommended oral dose level (in galantamine) of 12 mg, and in oral ER-unit forms at the maximal recommended oral dose level of 24 mg, and is orally administered alone at a maximal recommended daily dose level (in galantamine) of 24 mg.

Rivastigmine, as tartrate, was approved in oral IR-unit forms at the maximal recommended dose level (in rivastigmine) of 12 mg per day, given as two 6 mg doses (one in the morning and one in the evening), or as three 4mg doses (morning, noon, and evening) and, as free base, in ER-unit patch-form, at an initial daily dose of 4.6 mg/24 hours, at a daily tolerated dose of 9.5 mg/24 hour, and at the maximal recommended dose level of 13.3 mg/24 hours rivastigmine release.

In particular, rivastigmine is presented in capsules containing its hydrogen tartrate in amounts corresponding to 1.5, 3, 4.5 and 6 mg of rivastigmine base, as oral solution containing the tartrate corresponding to 2 mg of rivastigmine base and in form of a transdermal patch releasing rivastigmine at 4.6 mg/24 hours or 9.5 mg/24 hours, the recommended daily dosage for the IR forms being of from 6 to 12 mg, divided into 2 doses. The rivastigmine patch, Exelon®, is available as a 5 cm$^2$ patch, containing 9 mg rivastigmine, which delivers 4.6 mg rivastigmine in 24 hours, a 10 cm$^2$ patch containing 18 mg rivastigmine, which releases 9.5 mg/24 hours rivastigmine, and a 15 cm$^2$ patch containing 27 mg rivastigmine, that releases 13.3 mg/24 hours rivastigmine.

AChEIs vary in their pharmacological profiles and in their affinities for acetylcholinesterase and butyrylcholinesterase. Rivastigmine inhibits both acetylcholinesterase and butyrylcholinesterase enzymes with similar affinity (Thomsen et al., Life Scie. 1990, 46, 1553-58), which is incorporated herein by reference in its entirety.

Carefully conducted clinical trials of rivastigmine (Rösler et al., Brit. Med. J. 1999, 318, 633-38; Farlow et al. Eur. Neurol., 2000, 44, 236-41), which is herein incorporated by reference in its entirety, in patients with dementias of the Alzheimer type demonstrated small, but statistically significant, benefits on cognitive and global measures relevant to dementia. The magnitude of the effect in pivotal clinical trials was of the order of a 2.8 point improvement on the 70-point cognitive subscale of the Alzheimer's Disease Assessment Scale (ADAS-Cog), or 1-1.5 point improvement on the 30-point Mini-Mental Status Examination (MMSE) compared to placebo over six months.

Moreover, rivastigmine was given open-label to patients with Parkinson's disease (PD) at an initial dose of 1.5 mg twice a day and the dose was increased after 4 weeks to 3 mg twice daily, after 8 weeks to 4.5 mg twice daily and after 12 weeks to a maximal dose of 6 mg twice daily by trying to keep the dose of rivastigmine constant at the maximal 12 mg/day recommended dose, between weeks 12 and 26 of the trial. According to the Authors, rivastigmine may improve the cognitive functions in PD patients with dementia with no worsening of motor function. (Giladi et al., Acta Neurol Scand 2003, 108, 368-373), which is herein incorporated by reference in its entirety.

Unfortunately, however, none of the currently available medications offers more than modest clinical benefit for patients suffering from any of the aforementioned dementing disorders, even when these medications are administered at their maximum recommended dose. This is the first problem limiting the success of current AChEI therapy of Alzheimer type dementias.

A second problem limiting the success of current AChEI therapy of Alzheimer type dementias is that, even at recommended amounts, all these drugs produce dose limiting adverse reactions, mainly if not exclusively, by over-stimulating peripheral cholinergic receptors of the muscarinic type. As a result, signs and symptoms of untoward gastrointestinal, pulmonary, cardiovascular, urinary, and other systems dysfunction occur. These side effects commonly include, for rivastigmine, anorexia, nausea, vomiting, diarrhea, abdominal pain, weight loss; increased bronchial secretions, dyspnea, bronchoconstriction and bronchospasm; bradycardia, supraventricular cardiac conduction abnormalities, vasodilation, hypotension, dizziness and syncope; urinary bladder spasm, increased urinary frequency, and incontinence; flushing and diaphoresis; fatigue, headache, lacrymation, miosis, and loss of binocular vision (Physicians' Desk Reference 2008, Thomson PDR, Montvale, N.J.).

Adverse events attending the use of AChEIs appear to primarily reflect the excessive stimulation of peripheral cholinergic receptors, especially those of the muscarinic type (mAChRs). Five subtypes of muscarinic receptors, M1 through M5, have now been identified. Ongoing research has begun to map the distribution and physiologic role of these receptors as well as determine the binding affinity of drugs to them. For example, M1 receptors are found in sympathetic postganglionic neurons (autonomic ganglia), in gastric tissue and in the myenteric plexus; they are involved in secretions from salivary glands and the gastrointestinal tract. M2 receptors are present in cardiac and smooth muscle and have been implicated in the regulation of contractile forces of the atrial cardiac muscle and the conduction velocity of the atrioventricular node and thus heart rate. M2 receptors are also present on gastrointestinal smooth muscle as well as on detrusor smooth muscle cells and other structures within the bladder wall. M3 receptors are the predominant muscarinic receptor subtype mediating contraction of the stomach fundus, urinary bladder, and trachea. They are also expressed on glandular cells including gastric parietal cells and on vascular smooth muscle as well as detrusor smooth muscle and other structures within the bladder wall. M3 receptors are involved in exocrine gland secretion, smooth muscle contractility, emesis, pupil dilatation, food intake and weight gain.

It is also known that the degree to which AChEIs can attenuate the activity of this enzyme (acetylcholinesterase, AChE) in the CNS can be estimated by assays of AChE activity and related protein levels in the CSF and by use of cerebral imaging technology. It is reported that recommended maximal dose levels of these drugs typically achieve only less than 30% AChE inhibition (without a concomitant increase in AChE protein levels) in the CNS of Alzheimer disease patients (Kuhl et al, Ann Neurol Mar; 49[3]:416-417; Kaasinen V et al, Clin Psychopharmacol. 2002 December, 22[6]:615-20; Sinotoh et al. Curr Pharm Des, 2004; 10[13]:1505-17; Bohnen et al J Neurol Neurosurg Psychiatry, 2005 March; 76[3]:305; OtaT et al, Clin Neuropharmacol, 2010 March-April; 33[2]:74-8 ; Brannan S et al. ACNP 46th Annual Meeting, Program No. 4. Boca Raton Fla., Dec. 10, 2007—"Brannan 2007"; Farlow M et al AAN Poster 2008; Davidsson P et al Neurosci Lett 2001; 300:157-60; Amici S et al Mech Ageing Dev 2001; 122: 2057-62), the disclosures of which are each herein incorporated by reference in their entirety, and that inhibition of AChE activity and cognitive improvement are significantly correlated (Giacobini et al. J Neural Transm. 2002 July; 109(7-8):1053-65; Darreh-Shori T et al, J Neural Trans 2006; 113:1791-801), the disclosures of which are each herein incorporated by reference in their entirety, and that, ordinarily, a higher degree of enzyme blockade must be attained for maximum functional effect (Jann et al., Clin Pharmacokinet. 2002; 41(10):719-39—"Jann 2002"), the disclosure of which is herein incorporated by reference in its entirety.

An improvement in the treatment of Alzheimer type dementia is attained by a combined therapy associating a non-selective, peripheral anticholinergic agent, at a dose of from 20% to 200% the current daily doses, with an AChEI, at a dose up to about 4 times the maximal recommended dose of said AChEI, as disclosed in U.S. Pat. No. 8,404,701, the disclosure of which is herein incorporated by reference in its entirety. By such a treatment, a higher acetylcholinesterase inhibition in the CNS is achieved and greater relief of the symptoms of Alzheimer type dementia is enabled, by concomitantly decreasing concurrent adverse effects. Accordingly, for example, rivastigmine may be administered at a daily oral dose of up to 48 mg in combination with an nsPAChA.

In addition, U.S. Pat. No. 8,877,768, the disclosure of which is herein incorporated by reference in its entirety, discloses an improvement in the treatment of Alzheimer type dementia, which is attained by a combined therapy associating a non-anticholinergic-antiemetic agent, at a dose of from 50% to 300% the current IR daily doses, with an AChEI, at a dose up to 4 times the maximal recommended doses of said AChEI when administered alone.

Similarly, WO 2014/039637, the disclosure of which is herein incorporated by reference in its entirety, discloses the discovery of the property of the non-selective, peripheral anticholinergic agent of increasing the blood levels of a concurrently administered AChEI. Thus, this document recommends the use of high doses of both the non-selective, peripheral anticholinergic agent and of the AChEI in order to ameliorate the symptoms of Alzheimer's dementia. In particular, this document states that "[w]hile potentially lessening side effects and thereby enabling the use of higher and thus more effective doses of the AChEI, merely employing the concomitant use of antiemetics, such as domperidone and others, or of anticholinergics such as propantheline, oxybutynin, tolterodine and others, falls short of achieving the utmost therapeutic advantages of AChEIs in the treatment Alzheimer type dementias".

Thus, U.S. Pat. No. 8,404,701 and, especially, WO 2014/039637 specifically exclude anticholinergic agents which are selective and/or non-peripheral because selective agents are not able to counteract the whole spectrum of the AChEIs' adverse effect and, worse, the non-peripheral anticholinergics, such as oxybutynin, are able to dangerously counteract the beneficial central action of said AChEIs.

The literature discloses pharmaceutical compositions and Transdermal Therapeutic Systems (TTS) delivering oxybutynin through the human skin.

For example, U.S. Pat. Nos. 5,411,740 and 5,500,222, the disclosures of which are herein incorporated by reference in their entirety, disclose a patch for the transdermal administration of oxybutynin base using a monoglyceride or a mixture of monoglycerides of fatty acids as skin permeation-enhancer.

U.S. Pat. Nos. 5,686,097; 5,747,065; 5,750,137 and 5,900,250, the disclosures of which are herein incorporated by reference in their entirety, disclose a patch for the transdermal administration of oxybutynin base using a monoglyceride or a mixture of monoglycerides plus a lactate ester as skin permeation-enhancer.

A similar patch, adding a non-rate controlling tie layer on the skin-proximal surface of the reservoir, not affecting the drug release, is described in U.S. Pat. Nos. 5,614,211 and 5,635,203, the disclosures of which are herein incorporated by reference in their entirety.

U.S. Pat. Nos. 5,212,199, 5,227,169, 5,601,839 and 5,834,010, the disclosures of which are incorporated herein by reference in their entirety, disclose a patch for transdermal administration of basic drugs using triacetin as permeation enhancer.

U.S. Pat. No. 6,555,129, the disclosure of which is herein incorporated by reference in its entirety, discloses a TTS substantially consisting of an oxybutynin-containing matrix mass in the form of a layer which is self-adhesive, and in which the matrix mass consists of ammonium-group-containing (meth)acrylate copolymers, at least one citric acid triester and 5-25% by weight of oxybutynin.

U.S. Pat. No. 6,562,368, the disclosure of which is herein incorporated by reference in its entirety, discloses a method for transdermally administering oxybutynin using a composition in form of a patch, a cream, a gel, a lotion or a paste comprising oxybutynin and a hydroxide-releasing agent substantially consisting of inorganic hydroxides, inorganic oxides, metal salts of weak acids, and mixtures thereof.

U.S. Pat. Nos. 6,743,411; 7,081,249; 7,081,250; 7,081,251; 7,081,252 and 7,087,241, the disclosures of which are herein incorporated by reference in their entirety, disclose a transdermal patch delivering a composition comprising oxybutynin to a subject to provide a plasma area under the curve ratio of oxybutynin to an oxybutynin metabolite of from about 0.5:1 to about 5:1, optional in the presence of a permeation enhancer.

U.S. Pat. Nos. 7,029,694; 7,179,483; 8,241,662 and US 2009/0018190, the disclosures of which are herein incorporated by reference in their entirety, disclose a transdermal gel formulation comprising oxybutynin providing a plasma area under the curve ratio of oxybutynin to an oxybutynin metabolite of from about 0.5:1 to about 5:1, optional in the presence of a permeation enhancer.

US 2004/0219194, the disclosure of which is herein incorporated by reference in its entirety, discloses a transdermal therapeutic system containing oxybutynin, triacetin and *Aloe vera* extract as permeation enhancer.

US 2004/0057985, the disclosure of which is herein incorporated by reference in its entirety, discloses transdermal therapeutic systems (TTS) for the administration of oxybutynin with which therapeutically active absorption rates can be achieved without the necessity of adding permeation-enhancing substances. These TTS comprise a substantially water vapor-impermeable backing layer, at least one pressure-sensitive adhesive matrix layer attached thereto, and a detachable protective film, said matrix layer comprising an inner phase containing the active substance oxybutynin, and an outer, pressure sensitive adhesive phase based on hydrocarbon polymers or/and silicone polymers.

US 2005/0064037, the disclosure of which is herein incorporated by reference in its entirety, discloses an oxybutynin gel formulation topical gel formulation comprising oxybutynin chloride salt, a short chain alcohol, a gelling agent substantially consisting of high-molecular-weight, cross-linked polymer of acrylic acid or cross-linked copolymer of acrylic acid and C10-30 alkyl acrylate, and optionally a permeation enhancer substantially consisting of propylene glycol, propylene glycol laurate, isopropyl myristate, and methyl lactate.

WO 2005/039531, US2007/022379, US 2010/0216880, US 2014/0037713 and U.S. Pat. No. 8,652,491, the disclosures of which are herein incorporated by reference in their entirety, disclose a transdermal or transmucosal pharmaceutical formulation, that can be utilized for topical or transdermal application, such that solutions, creams, lotions, sprays, ointment, gels, aerosols and patch devices, for the delivery of one or more active agents, including anticholinergics, in particular oxybutynin. Said formulation includes oxybutynin in a solvent system comprising a diethylene glycol monoalkyl ether and a glycol in specific ratios, alcohol and water. In particular, according to U.S. Pat. No. 8,652,491 a possible secondary active agent, in addition to the anti-cholinergic agent such as oxybutynin, may be an antiperspirant, a tranquilizer or another agent capable of ameliorating hyperhidrosis.

WO 2005/107812, U.S. Pat. No. 7,425,340 and US 2008/0260842, the disclosures of which are herein incorporated by reference in their entirety, disclose formulations containing an anticholinergic agent, in particular oxybutynin, in admixture with urea, urea congeners or urea-containing compounds as permeation enhancers.

WO 01/07018 and U.S. Pat. No. 8,420,117, the disclosures of which are herein incorporated by reference in their entirety, disclose a matrix patch formulation containing no water for external use, comprising, as essential components oxybutynin hydrochloride, citric acid and sodium acetate.

WO2013/061969 and US 2014/0271796, the disclosures of which are herein incorporated by reference in their entirety, disclose a transdermal absorption preparation comprising at least one drug selected from oxybutynin and pharmaceutically acceptable salts thereof; and a sterol such as cholesterol, cholesterol derivatives and cholesterol analogs.

U.S. Pat. No. 8,802,134, the disclosure of which is herein incorporated by reference in its entirety, discloses a method for producing a patch wherein oxybutynin is incorporated in an adhesive agent layer composition comprises the acrylic-based polymer as the adhesive base agent, and the acrylic-based polymer is a copolymer of polymethyl methacrylate with a polyacrylate.

U.S. Pat. No. 8,877,235, the disclosure of which is herein incorporated by reference in its entirety, discloses a patch consisting of a support layer and of an adhesive agent layer arranged on the at least one surface of the support layer, the adhesive agent layer comprising oxybutynin hydrochloride in a supersaturated concentration in a dissolved form. Said layer also comprises acrylic-based polymers and rubber-based polymers, as adhesive base agents, and liquid paraffin, a sterol, an organic acid, and a tackifier.

The disclosures of the aforementioned documents are incorporated herein by reference in their entirety.

Oxybutynin is a well-known non-selective anticholinergic medication used to relieve urinary and bladder difficulties, including frequent urination and urge incontinence and all the above references emphasize this use. However, as set forth above, oxybutynin is not "peripheral" as per the definition given above because it is able to cross the blood brain barrier ("BBB") to a non-negligible extent (Rebecca J McCrery and Rodney A Appell, Ther Clin Risk Manag. March 2006; 2/1: 19-24).

Oxybutynin is commercially presented in a 39-cm$^2$ patch system containing 36 mg of oxybutynin and releasing 3.9 mg/day oxybutynin (OXYTROL®). This patch provides significant improvements in all the measured parameters with less systemic adverse effects, as summarized by J. Jayarajan and S. B. Radomski in a review presented on 4 Dec. 2013: "Pharmacotherapy of overactive bladder in adults: a review of efficacy, tolerability, and quality of life" (J. Jayarajan et al., Research and Reports in Urology 2014: 6), the disclosure of which is herein incorporated by reference in its entirety. However, oxybutynin is anyway deemed to cross the BBB owing to its high lipophilicity, neutrality, and small molecular size (C. A. Donnellan et al. BMJ 1997; 315:1363-4; R. Scheife and M. Takeda, Clin Ther. 2005; 27:144-53). the disclosure of which is herein incorporated by reference in its entirety.

Oxybutynin is also commercially presented (GELNIQUE®) in a TTS consisting of a hydroalcoholic gel containing 100 mg oxybutynin chloride per gram of gel and available in a 1 gram (1.14 ml) unit dose. This TTS is deemed to have a pharmacokinetic profile similar to that of the patch delivery system, while producing lower N-desethyloxybutynin metabolite plasma concentrations (Vincent R Lucente et al.; Open Access Journal of Urology 2011/3, 35-42). Another commercial TTS system, presents oxybutynin in a hydroalcoholic gel containing 30 mg oxybutynin base per gram of gel and is available (ANTUROL®) in a 0.92 gram (1 mL) unit dose that contains 28 mg oxybutynin per gram of gel. Also Anturol® demonstrated plasma levels of oxybutynin comparable to the efficacious plasma levels observed for oral and patch therapies with lower N-desethyloxybutynin plasma levels (Anturol® Gel Summary by Antares Pharma).

Oxybutynin is a very good tool for administering anticholinergic therapy. Administered orally to mice, it has been shown to cross the Blood-Brain-Barrier. Even when given by transdermal route, oxybutynin has been shown to penetrate the brain. Studies with radiolabeled [14C] oxybutynin administered transdermally to rats have shown presence of radiolabel in the brain [Pharmaceutical and Medical Devices Agency Interview Form (PMDA is the Japanese Regultaory Agency, equivalent to FDA in the US]. The label for transdermal oxybutynin warns that a variety of CNS anticholinergic effects have been reported, including headache, dizziness, and somnolence. Patients should be monitored for signs of anticholinergic CNS effects, particularly after beginning treatment. The label further advises that patients should be told not to drive or operate heavy machinery until they know how transdermal oxybutynin affects them. The label also advises that if a patient experiences anticholinergic CNS effects, drug discontinuation should be considered. In addition, the label states that overdosage with oxybutynin has been associated with CNS anticholinergic effects including excitation, memory loss, stupor, disorientation and agitation on awakening. Hence, based on the existing literature, and the competing action of oxybutynin and an AChEI in the CNS, the combined use of such drugs would have made memory loss a-priori material risk for the treatment of Alzheimer type dementia.

SUMMARY OF THE INVENTION

It has now been found that the combination of an oxybutynin TTS, in particular as a patch, and rivastigmine at high doses, surprisingly provides unexpected results: oxybutynin does not induce any dose-limiting adverse effect; and the very high doses of rivastigmine do not induce any dose-limiting adverse effect.

It has also been found that it is possible to administer high doses of rivastigmine in combination with currently available oxybutynin transdermal therapeutic system without inducing rivastigmine-associated dose-limiting adverse effects due to the concurrent presence of oxybutynin in the combination. In addition, it has been found that oxybutynin unexpectedly enables the use of doses of AChEIs that are much higher than the doses of AChEIs that are possible even with the usual peripheral anticholinergic therapies.

In particular, it has been found that a sole patch releasing 3.9 mg/day oxybutynin allows the concurrent, safe use of up to at least 6 patches each releasing 4.6 mg/24 hours rivastigmine in human beings, without any relevant sign of dose-limiting peripheral, rivastigmine-induced cholinergic adverse effects or dose-limiting oxybutynin-induced anticholinergic effects. This finding revealed the opportunity of using an oxybutynin transdermal therapeutic system for administering up to 10 times the maximal recommended rivastigmine patch or gel daily dose.

This finding was unexpected in view of the disclosures of the prior art. In fact, the treated subjects did not evidence signs of the rivastigmine peripheral cholinergic side effects notwithstanding the high rivastigmine doses and also tolerated said high rivastigmine doses notwithstanding the relatively low oxybutynin administered dose (100% of that used in the anticholinergic therapy), compared with the high anticholinergic doses used for example, in WO 2014/039637.

In addition, the treated subjects did not show any sign of central anticholinergic adverse effects such as mental or mood changes (e.g., confusion or memory loss, somnolence or convulsions. Thus, the finding of the present invention led to the unexpected conclusion that an oxybutynin patch can be used to antagonize the adverse effects of rivastigmine (and most likely of any AChEI such as huperzine A, tacrine, galantamine and donepezil) without bad effects for example on cognition. In particular, said oxybutynin patch may be for use in the treatment of patients suffering from Alzheimer type dementia without worsening the cognition of said patients.

Thus, the present invention provides a pharmaceutical combination comprising
  (a) oxybutynin or a pharmaceutically acceptable salt thereof in a TTS; and
  (b) an AChEI.

This combination is useful for a safe treatment of hypocholinergic disorders such as Alzheimer type dementia whereby, on one side, the AChEI action does not involve appreciable adverse effects and, on the other side, oxybutynin surprisingly does not involve adverse effects in the CNS.

According to an embodiment, the present invention provides a pharmaceutical combination comprising (a) oxybutynin or a pharmaceutically acceptable salt thereof in a TTS and (b) an AChEI selected from the group consisting of huperzine A, tacrine, donepezil, galantamine, rivastigmine, and pharmaceutically acceptable salts thereof.

According to another embodiment, Component (b) is AChEI selected from the group consisting of huperzine A, in an amount, per single dose, of from 0.3 mg to 2.0 mg; tacrine and pharmaceutically acceptable salts thereof, in an amount in tacrine, per single dose, of from 60 mg to 400 mg; donepezil and pharmaceutically acceptable salts thereof, in an amount, per single dose, corresponding to from 15 mg to 100 mg of donepezil hydrochloride; galantamine and pharmaceutically acceptable salts thereof, in an amount in galantamine, per single dose, of from 18 mg to 120 mg; and rivastigmine and pharmaceutically acceptable salts thereof in an amount in rivastigmine, per single dose, of from 9 mg to 60 mg.

Such a combination is a new tool for treating hypocholinergic disorders such as Alzheimer type dementia. Said new tool comprises treating a patient in need of such a treatment with a transdermal therapeutic system comprising oxybutynin, in combination with oral or transdermal AChEIs, such as preferably, rivastigmine at daily doses of from 13.20 mg to 120 mg, preferably from 13.20 mg to 108 mg, preferably from 13.20 mg to 96 mg, preferably from 13.20 mg to 84 mg, preferably from 13.20 mg to 72 mg, preferably from 13.20 mg to 60 mg, preferably from 13.20 mg to 48 mg, preferably from 13.20 mg to 36 mg, preferably from 13.20 mg to 24 mg, or in patch releasing from 5.06 mg/24 h to 46 mg/24 h rivastigmine, from 10.45 mg/24 h to 95 mg/24 h, or from 14.63 mg/24 to 119.7 mg/24 h. This treatment occurs, on one hand without the onset of dose-limiting rivastigmine cholinergic peripheral adverse effects and, on the other hand, without the onset of oxybutynin dose-limiting anticholinergic central adverse effects.

According to the present invention, it is also possible to equilibrate the transdermal oxybutynin dose and the oral or transdermal rivastigmine doses in order to attain the maximum efficacy with reduced risk of both central and peripheral adverse effects, by using a transdermal therapeutic system containing a predetermined dose of oxybutynin or a pharmaceutically acceptable salt thereof, concurrently with a predetermined daily dose of rivastigmine or of a pharmaceutically acceptable salt thereof.

An embodiment of the invention relates to a method for treating hypocholinergic disorders such as Alzheimer type dementia, which comprises daily administering to a patient in need of said treatment a transdermal therapeutic system comprising oxybutynin or pharmaceutically acceptable salt thereof in combination with a cholinesterase inhibitor selected from the group consisting of rivastigmine or pharmaceutically acceptable salt thereof, in which the amount of rivastigmine is from 5.06 mg/24 h to 46 mg/24 h rivastigmine, from 10.45 mg/24 h to 95 mg/24 h, or from 14.63 mg/24 to 119.7 mg/24 h.

In one embodiment of the method, the oxybutynin in the transdermal therapeutic system is in a patch delivering oxybutynin at a rate of 3.9 mg/24 hours and the rivastigmine in the transdermal therapeutic system is in patch globally delivering rivastigmine at a rate from 5.06 mg/24 h to 18.4 mg/24 h, from 5.06 mg/24 h to 23 mg/24 h, from 5.06 mg/24 h to 27.6 mg/24 h, from 5.06 mg/24 h to 32.20 mg/24, up to 46 mg/24 h. Preferably, the rivastigmine in the transdermal therapeutic system is in patch globally delivering rivastigmine at a rate from greater than 27.6 mg/24 h, from greater than 32.2 mg/24 h, from greater than 36.8 mg/24 h, from greater than 41.40 mg/24 h, up to 46 mg/24 h.

In another embodiment of the method, the oxybutynin in the transdermal therapeutic system is in patch delivering oxybutynin at a rate of from 3.9 mg/24 hours to 5.85 mg/24 hours and the rivastigmine in the transdermal therapeutic system is in patch globally delivering rivastigmine at a rate from 10.45 mg/24 h to 38 mg/24 h, from 10.45 mg/24 h to 47.5 mg/24 h, from 10.45 mg/24 h to 57 mg/24 h, from 10.45 mg/24 h to 66.5 mg/24 h, up to 95 mg/24 h. Preferably, the rivastigmine in the transdermal therapeutic system is in patch globally delivering rivastigmine at a rate from greater than 57 mg/24 h, from greater than 66.5 mg/24 h, from greater than 76 mg/24 h, from greater than 85.5 mg/24 h, up to 95 mg/24 h.

In another embodiment of the method, the oxybutynin in the transdermal therapeutic system is in patch delivering oxybutynin at a rate of from 3.9 mg/24 hours to 7.8 mg/24 hours and the rivastigmine in the transdermal therapeutic system is in patch globally delivering rivastigmine at a rate from 14.63 mg/24 h to 53.2 mg/24 h, from 14.63 mg/24 h to 66.5 mg/24 h, from 14.63 mg/24 h to 79.8 mg/24 h, from 14.63 mg/24 h to 93.10 mg/24 h, up to 119.7 mg/24 h. Preferably, the rivastigmine in the transdermal therapeutic system is in patch globally delivering rivastigmine at a rate from greater than 79.8 mg/24 h, from greater than 93.10 mg/24 h, from greater than 106.4 mg/24 h, up to 119.7 mg/24 h.

In one embodiment of the method, the transdermal therapeutic system delivers oxybutynin at a rate of 3.9 mg/24 hours and is combined with an oral daily dose of rivastigmine hydrogen tartrate from 18 mg to 36 mg.

Another embodiment of the invention relates to a transdermal therapeutic system comprising oxybutynin or pharmaceutically acceptable salt thereof in combination with an acetyl choline esterase inhibitor (AChEI) at a high dose level, per single dose, that may be higher than the maximum recommended single dose, in particular from 1.5 to 10 times higher than a recommended maximal single dose level, from 1.5 to 9 times higher than a recommended maximal single dose level, from 1.5 to 8 times higher than a recommended maximal single dose level, from 1.5 to 7 times higher than a recommended maximal single dose level, from 1.5 to 6 times higher than a recommended maximal single dose level, from 1.5 to 5 times higher than a recommended maximal single dose level, from 1.5 to 4 times higher than a recommended maximal single dose level, from 1.5 to 3 times higher than a recommended maximal single dose level, or from 1.5 to 2 times higher than a recommended maximal single dose level. More preferably, the dose is from greater than 6 to 10 times higher than a recommended maximal single dose level, from greater than 7 to 10 times higher than a recommended maximal single dose level, from greater than 8 to 10 times higher than a recommended maximal single dose level, from greater than 9 to 10 times higher than a recommended maximal single dose level, or 10 times higher than a recommended maximal single dose level. Said dose level refers to an AChEI dose in a unit form for oral use, as illustrated above.

In yet another embodiment, the invention relates to a transdermal therapeutic system comprising oxybutynin or pharmaceutically acceptable salt thereof in combination with an acetyl choline esterase inhibitor (AChEI) at a high dose level. that may be higher than the maximum recommended daily dose, in particular from 1.5 to 10 times higher than a recommended maximal daily dose level, from 1.5 to 9 times higher than a recommended maximal daily dose level, from 1.5 to 8 times higher than a recommended maximal daily dose level, from 1.5 to 7 times higher than a recommended maximal daily dose level, from 1.5 to 6 times higher than a recommended maximal daily dose level, from 1.5 to 5 times higher than a recommended maximal daily dose level, from 1.5 to 4 times higher than a recommended maximal daily dose level, from 1.5 to 3 times higher than a recommended maximal daily dose level, or from from 1.5 to 2 times higher than a recommended maximal daily dose level. More preferably, the dose is from greater than 6 to 10 times higher than a recommended maximal daily dose level, from greater than 7 to 10 times higher than a recommended maximal daily dose level, from greater than 8 to 10 times higher than a recommended maximal daily dose level, from greater than 9 to 10 times higher than a recommended maximal daily dose level, or 10 times higher than a recommended maximal daily dose level.

In one embodiment of the transdermal therapeutic system, the oxybutynin or pharmaceutically acceptable salt thereof is in patch transdermal formulation.

In another embodiment of the transdermal therapeutic system, the AChEI is rivastigmine or pharmaceutically acceptable salt thereof, and the rivastigmine or pharmaceutically acceptable salt thereof is in a transdermal formulation or in a form for oral administration.

In an embodiment of the transdermal therapeutic system, the transdermal formulation for each of oxybutynin or pharmaceutically acceptable salt thereof and rivastigmine or pharmaceutically acceptable salt thereof is incorporated into a patch.

In another embodiment of the transdermal therapeutic system, the oxybutynin or pharmaceutically acceptable salt thereof is in a transdermal formulation incorporated into a patch, and the rivastigmine or pharmaceutically acceptable salt thereof is in an oral dosage form.

DETAILED DESCRIPTION

The present invention provides an oxybutynin-based transdermal therapeutic system that may be used for the treatment of hypocholinergic disorders of the central nervous system, including but not limited to Alzheimer disease, Alzheimer type dementia (including but not limited to Parkinson's disease dementia, Lewy Body Disease dementia, Frontotemporal degeneration, Fronto temporal lobar dementia), Mild cognitive impairment, post-stroke dementia, Vascular dementia, Traumatic Brain Injury, Down Syndrome, Tourette syndrome, tardive dyskinesia, Pick's disease, Huntington's chorea, Friedrich's ataxia, falls, Anorexia nervosa, and Schizophrenia, including schizophrenia-associated dementia and schizoaffective disorders.

In particular, the present invention provides a transdermal therapeutic system comprising oxybutynin, or a pharmaceutically acceptable salt thereof, for its use in the treatment of dementia of Alzheimer type, in combination with an AChEI orally or transdermally administered at a high dose, in particular a dose of AChEI from 1.1 times to 4 times higher than the daily maximal recommended oral or transdermal dose, from 1.1 times to 5 times higher than the daily maximal recommended oral or transdermal dose, from 1.1 times to 6 times higher than the daily maximal recommended oral or transdermal dose, from 1.1 times to 7 times higher than the daily maximal recommended oral or transdermal dose, from 1.1 times to 8 times higher than the daily maximal recommended oral or transdermal dose, from 1.1 times to 9 times higher than the daily maximal recommended oral or transdermal dose, or from 1.1 times to 10 times higher than the daily maximal recommended oral or transdermal dose.

In another embodiment, the present invention provides a transdermal therapeutic system comprising oxybutynin, or a pharmaceutically acceptable salt thereof, for its use in the treatment of dementia of Alzheimer type, in combination with an AChEI administered at a high dose, in particular a dose of AChEI that is from greater than 1.1 times higher than the daily maximal recommended or transdermal dose, a dose of AChEI that is from greater than 1.5 times higher than a daily maximal recommended or transdermal dose, a dose of AChEI that is from greater than 2 times higher than a daily maximal recommended or transdermal dose, a dose of AChEI that is from greater than 3 times higher than a daily maximal recommended or transdermal dose, a dose of AChEI that is from greater than 4 times higher than a daily maximal recommended or transdermal dose, a dose of AChEI that is from greater than 5 times higher than a daily maximal recommended or transdermal dose, a dose of AChEI that is from greater than 6 times higher than a daily maximal recommended or transdermal dose, a dose of AChEI that is from greater than 7 times higher than a daily maximal recommended or transdermal dose, a dose of AChEI that is from greater than 8 times higher than a daily maximal recommended or transdermal dose, a dose of AChEI that is from greater than 9 times higher than a daily maximal recommended or transdermal dose, or a dose of AChEI that is 10 times higher than a daily maximal recommended or transdermal dose. More preferably, the dose is from greater than 6 times higher than a daily maximal recommended oral or transdermal dose, from greater than 7 times higher than a daily maximal recommended oral or transdermal dose, from greater than 8 times higher than a daily maximal recommended oral or transdermal dose, from greater than 9 times higher than a daily maximal recommended oral or transdermal dose, or 10 times higher than a daily maximal recommended oral or transdermal dose. Even more preferably, the dose is from greater than 6 to 10 times higher than a daily maximal recommended oral or transdermal dose, from greater than 7 to 10 times higher than a daily maximal recommended oral or transdermal dose, from greater than 8 to 10 times higher than a daily maximal recommended oral or transdermal dose, from greater than 9 to 10 times higher than a daily maximal recommended oral or transdermal dose.

In yet another embodiment, the present invention provides a transdermal therapeutic system comprising oxybutynin, or a pharmaceutically acceptable salt thereof, for its use in the treatment of dementia of Alzheimer type, in combination with an AChEI at a dose higher or greater than a maximal tolerated dose currently used in AChEI therapy for Alzheimer type dementia. In particular a dose of AChEI that is from 1.1 to 10 times higher than the maximal tolerated dose, a dose of AChEI that is from 1.5 to 10 times higher than the maximal tolerated dose, a dose of AChEI that is from 2 to 10 times higher than the maximal tolerated dose, a dose of AChEI that is from 3 to 10 times higher than the maximal tolerated dose, a dose of AChEI that is from 4 to 10 times higher than the maximal tolerated dose, a dose of AChEI that is from 5 to 10 times or higher than the maximal tolerated dose, a dose of AChEI that is from 6 to 10 times higher than the maximal tolerated dose, a dose of AChEI that is from 7 to 10 times higher than the maximal tolerated dose, a dose of AChEI that is from 8 times to 10 higher than the maximal tolerated dose, a dose of AChEI that is from 9 to 10 times higher than the maximal tolerated dose, or a dose of AChEI that is 10 times higher than the maximal tolerated dose, currently used in AChEI therapy for Alzheimer type dementia.

In another embodiment, the present invention provides a transdermal therapeutic system comprising oxybutynin, or a pharmaceutically acceptable salt thereof, for its use in the treatment of dementia of Alzheimer type, in combination with an AChEI at a dose higher or greater than a maximal tolerated dose currently used in AChEI therapy for Alzheimer type dementia. In particular a dose of AChEI that is from greater than 1.1 times higher than the maximal tolerated dose, a dose of AChEI that is from greater than 1.5 times higher than the maximal tolerated dose, a dose of AChEI that is from greater than 2 times higher than the maximal tolerated dose, a dose of AChEI that is from greater than 3 times higher than the maximal tolerated dose, a dose of AChEI that is from greater than 4 times higher than the maximal tolerated dose, a dose of AChEI that is from greater than 5 times higher than the maximal tolerated dose, a dose of AChEI that is from greater than 6 times higher than the maximal tolerated dose, a dose of AChEI that is from greater than 7 times higher than the maximal tolerated dose, a dose of AChEI that is from greater than 8 times higher than the maximal tolerated dose, a dose of AChEI that is from greater than 9 times higher than the maximal tolerated dose, or a dose of AChEI that is 10 times higher than the maximal tolerated dose, currently used in AChEI therapy for Alzheimer type dementia. More preferably, the dose of AChEI is from greater than 6 times higher than the maximal tolerated dose, a dose of AChEI that is from greater than 7 times higher than the maximal tolerated dose, a dose of AChEI that is from greater than 8 times higher than the maximal tolerated dose, a dose of AChEI that is from greater than 9 times higher than the maximal tolerated dose, or a dose of AChEI that is 10 times higher than the maximal tolerated dose, currently used in AChEI therapy for Alzheimer type dementia.

Even more preferably, the dose is from greater than 6 to 10 times higher than a maximal tolerated dose, from greater than 7 to 10 times higher than a maximal tolerated dose, from greater than 8 to 10 times higher than a maximal tolerated dose, from greater than 9 to 10 times higher than a maximal tolerated dose, currently used in AChEI therapy for Alzheimer type dementia.

In another embodiment, the invention provides a transdermal therapeutic system comprising oxybutynin or pharmaceutically acceptable salt thereof in combination with an acetyl choline esterase inhibitor (AChEI) at a high dose level, per single dose, that may be higher than the maximum recommended single dose, in particular from 1.5 to 10 times higher than a recommended maximal single dose level, from 1.5 to 9 times higher than a recommended maximal single dose level, from 1.5 to 8 times higher than a recommended maximal single dose level, from 1.5 to 7 times higher than a recommended maximal single dose level, from 1.5 to 6 times higher than a recommended maximal single dose level, from 1.5 to 5 times higher than a recommended maximal single dose level, from 1.5 to 4 times higher than a recommended maximal single dose level, from 1.5 to 3 times higher than a recommended maximal single dose level, or from from 1.5 to 2 times higher than a recommended maximal single dose level. More preferably, the dose is from greater than 6 to 10 times higher than a recommended maximal single dose level, from greater than 7 to 10 times higher than a recommended maximal single dose level, from greater than 8 to 10 times higher than a recommended maximal single dose level, from greater than 9 to 10 times higher than a recommended maximal single dose level, or 10 times higher than a recommended maximal single dose level.

In yet another embodiment, the invention provides a transdermal therapeutic system comprising oxybutynin or pharmaceutically acceptable salt thereof in combination with an acetyl choline esterase inhibitor (AChEI) at a high dose level, that may be higher than the maximum recommended daily dose, in particular from 1.5 to 10 times higher than a recommended maximal daily dose level, from 1.5 to 9 times higher than a recommended maximal daily dose level, from 1.5 to 8 times higher than a recommended maximal daily dose level, from 1.5 to 7 times higher than a recommended maximal daily dose level, from 1.5 to 6 times higher than a recommended maximal daily dose level, from 1.5 to 5 times higher than a recommended maximal daily dose level, from 1.5 to 4 times higher than a recommended maximal daily dose level, from 1.5 to 3 times higher than a recommended maximal daily dose level, or from from 1.5 to 2 times higher than a recommended maximal daily dose level. More preferably, the dose is from greater than 6 to 10 times higher than a recommended maximal daily dose level, from greater than 7 to 10 times higher than a recommended maximal daily dose level, from greater than 8 to 10 times higher than a recommended maximal daily dose level, from greater than 9 to 10 times higher than a recommended maximal daily dose level, or 10 times higher than a recommended maximal daily dose level.

The oxybutynin TTS may contain oxybutynin or a pharmaceutically acceptable salt thereof in an amount allowing an oxybutynin release of 3.9 mg/24 h, or from 3.9 mg/24 h to 5.85 mg/24 h or from 3.9 mg/24 h to 7.8 mg/24 h. This use is rendered possible by the combination of oxybutynin, in a transdermal therapeutic system, with an acetylcholinesterase inhibitor (AChEI) such as those mentioned above, in particular with huperzine A, tacrine, donepezil, galantamine, rivastigmine, and pharmaceutically acceptable salts thereof, said AChEI being present in said combination at doses higher than the currently approved dose levels, in particular at doses up to 4 times, or higher than 4 times, preferably higher than 6 times, the currently approved doses.

In this combination, the transdermal form of oxybutynin may be combined with AChEI doses that would not be tolerated or are criticized for their questionable benefit/risk ratio, as it happens in the case of 23-mg donepezil.

According to the present invention, the donepezil 23-mg dose may be administered chronically without any dose-limiting adverse effect, if combined with oxybutynin in a TTS formulation.

Thus, the present invention provides a pharmaceutical combination comprising, as Components:
  (a) oxybutynin or a pharmaceutically acceptable salt thereof, in a transdermal therapeutic system; and
  (b) an AChEI.

According to an advantageous embodiment, in said combination the AChEI Component (b) is selected from the group consisting of huperzine A; tacrine and pharmaceutically acceptable salts thereof, preferably its hydrochloride; donepezil and pharmaceutically acceptable salts thereof, preferably its hydrochloride; galantamine and pharmaceutically acceptable salts thereof, preferably its hydrobromide; and rivastigmine and pharmaceutically acceptable salts thereof, preferably its hydrogen tartrate.

Thus, the invention provides a pharmaceutical combination comprising, as Components:
  (a) oxybutynin or a pharmaceutically acceptable salt thereof, in a transdermal therapeutic system; and
  (b) an acetyl choline esterase inhibitor (AChEI) selected form the group consisting of huperzine A, in an amount, per single dose, of from 0.22 mg to 2.0 mg; tacrine and pharmaceutically acceptable salts thereof, in an amount, per single dose, of from 44 mg to 400 mg; donepezil and pharmaceutically acceptable salts thereof, in an amount, per single dose, of from 11 mg to 100 mg, preferably from 11.0 to 70 mg; galantamine and pharmaceutically acceptable salts thereof, in an amount, per single dose, of from 13.20 mg to 240 mg; and rivastigmine and pharmaceutically acceptable salts thereof, in an amount, per single dose, of from 9 mg to 120 mg.

For example, in this combination, galantamine, or a pharmaceutically acceptable salt thereof, is present, in general as hydrobromide, in an amount of from 18 mg to 48 mg per single oral dose in IR-formulation or in an amount (in galantamine) of from 36 mg to 96 mg per single oral dose in oral ER-formulation.

Rivastigmine, or a pharmaceutically acceptable salt thereof, may be present in this combination in an amount (in rivastigmine) of from 9 mg to 24 mg per single oral dose, in oral IR-formulation or, in patch releasing from 14.1 mg/24 h to 53.2 mg/24 h, normally from 14.1 mg/24 h to 46 mg/24 h, more advantageously in some cases from 14.1 mg/24 h to 38 mg/24 h, from 18.4 mg/24 hours to 28.5 mg/24 hours, preferably from 19 mg/24 hours to 28.5 mg/24 hours rivastigmine.

Donepezil hydrochloride may be present in the combination in an amount, per single dose, of from 15 mg to 92 mg, of from 15 mg to 60 mg, advantageously from 23 mg to 70 mg, more advantageously from 25 mg to 60 mg, normally from 15 mg to 40 mg, generally in IR formulation.

In general, the oxybutynin-based TTS Component (a) may be an occlusive or non-occlusive system such as a patch containing oxybutynin as active agent, said patch transdermally releasing a predetermined amount of oxybutynin, or a pharmaceutical composition comprising oxybutynin or a pharmaceutically acceptable salt thereof such as its hydrochloride, in admixture with a pharmaceutical carrier, said composition being in form of topical cream, gel or sprayable solution transdermally delivering a predetermined amount of oxybutynin. According to a preferred embodiment, said oxybutynin-based TTS is a patch delivering from 3.9 mg/24 h to 7.8 mg/24 h, normally from 3.9 mg/24 h to 5.85 mg/24 h.

In said combination, said AChEI Component (b) may be formulated, in admixture with a pharmaceutical carrier or vehicle, in a pharmaceutical composition or device in dosage unit form. According to a preferred embodiment, said composition or device comprises an AChEI selected from the group consisting of huperzine A, in an amount of from 0.3 mg to 0.8 mg, in admixture with a pharmaceutical carrier in an oral IR formulation; donepezil hydrochloride, in an amount of from 25 mg to 92 mg, in admixture with a pharmaceutical carrier in an oral IR-formulation; galantamine, as hydrobromide, in an amount of from 18 mg to 48 mg, in admixture with a pharmaceutical carrier in an oral IR-formulation; galantamine, as hydrobromide, in an amount of from 36 mg to 96 mg, in admixture with a pharmaceutical carrier in an oral ER-formulation; rivastigmine, as hydrogen tartrate, in an amount of from 9 mg to 24 mg, in admixture with a pharmaceutical carrier in an oral IR-formulation; and rivastigmine, in patch releasing from 14.1 mg to 53.2 mg/24 h of rivastigmine.

An advantageous pharmaceutical combination comprises Component (a), consisting of oxybutynin or a pharmaceutically acceptable salt thereof, formulated in a TTS delivering oxybutynin at a dose of from 3.9 mg/24 h to 7.8 mg/24 h, in particular from 3.9 mg/24 h to 5.85 mg/24 h or of 3.9 mg/24 h; and Component (b), consisting of donepezil hydrochloride, in an oral pharmaceutical composition comprising said donepezil hydrochloride in an amount of from 15 mg to 92 mg, in particular from 23 mg to 70 mg, from 25 mg to 60 mg or from 15 mg to 40 mg, in admixture with a pharmaceutical carrier.

Another advantageous combination comprises Component (a), consisting of a TTS delivering oxybutynin at a dose of 3.9 mg/24 h, and said Component (b) is donepezil hydrochloride in a 23-mg oral formulation, said TTS being a patch.

A further advantageous combination comprises Component (a), consisting of a TTS delivering oxybutynin at a dose of from 3.9 mg/24 h to 7.8 mg/24 h, and said Component (b) is galantamine hydrobromide, in an amount of from 48 mg to 96 mg in an oral ER-formulation, said TTS being a patch.

According to an embodiment, the invention provides a combination of an oxybutynin-based TTS delivering from 3.9 mg/24 h to 7.8 mg/24 h, normally from 3.9 to 5.85 mg/24 h of oxybutynin, as Component (a), with rivastigmine, in patch releasing from 14.1 mg/24 h to 46 mg/24 h of rivastigmine, as Component (b).

According to another embodiment, the invention provides a combination of an oxybutynin-based patch releasing 3.9 mg/24 h of active agent, as Component (a), with rivastigmine, in patch globally releasing from 14.1 mg/24 h to 28.5 mg/24 h, advantageously from 19 mg/24 h to 28.5 mg/24 h of active agent, as Component (b). For example, as set forth above, a combination of this oxybutynin patch, as Component (a) with rivastigmine, in patch globally delivering rivastigmine at a rate from 14.1 mg/24 hours to 27.6 mg/24 h, as Component (b), is perfectly tolerated. Thus, the high amount of the rivastigmine-released doses is highly predictive for an improvement of the cognitive conditions of patients suffering from a hypocholinergic disorders such as mild or moderate dementia of Alzheimer type.

The present invention further provides a transdermal therapeutic system comprising oxybutynin, or a pharmaceutically acceptable salt thereof, for its use in the treatment of hypocholinergic disorders such as dementia of Alzheimer type, in combination with an AChEI orally or transdermally administered at a high dose, in particular at an AChEI dose that may be up to 4 times higher than the maximal recommended daily dose level, in particular as high as from 1.5 times to 4 times the daily maximal recommended dose when said AChEI is administered orally. In another embodiment, an AChEI dose that may be from greater than 4 times higher than the maximal recommended daily dose level or maximal tolerated dose, from greater than 5 times higher than the maximal recommended daily dose level or maximal tolerated dose, from greater than 6 times higher than the maximal recommended daily dose level or maximal tolerated dose, from greater than 7 times higher than the maximal recommended daily dose level or maximal tolerated dose, from greater than 8 times higher than the maximal recommended daily dose level or maximal tolerated dose, from greater than 9 times higher than the maximal recommended daily dose level or maximal tolerated dose, or of 10 times higher than the maximal recommended daily dose level or maximal tolerated dose; when said AChEI is administered orally.

Preferably, the AChEI is rivastigmine.

The oxybutynin TTS may contain oxybutynin or a pharmaceutically acceptable salt thereof in an amount allowing an oxybutynin release of from 3.9 mg/24 h to 7.8 mg/24 h, normally of 3.9 mg/24 h, or from 3.9 mg/24 h to 5.85 mg/24 h.

In combination with the aforementioned oxybutynin TTS, rivastigmine is administered at a daily dose of from 5.06 mg to 93.1 mg. Rivastigmine, as rivastigmine hydrogen tartrate, is administered orally at a daily dose of from 15 mg, preferably from 18 mg, to 84 mg, or transdermally in a TTS releasing from 5.06 mg/24 h to 46 mg/24 h rivastigmine, from 10.45 mg/24 h to 95 mg/24 h, or from 14.63 mg/24 to 119.7 mg/24 h. Preferably, the rivastigmine, as a rivastigmine hydrogen tartrate, is administered transdermally in the TTS is releasing greater than from 27.6 mg/24 h, greater than from 32.2 mg/24 h, greater than from 36.8 mg/24 h, greater than from 41.40 mg/24 h, up to 46 mg/24 h; from 10.45 mg/24 h to 38 mg/24 h, from 10.45 mg/24 h to 47.5 mg/24 h, from 10.45 mg/24 h to 57 mg/24 h, from 10.45 mg/24 h to 66.5 mg/24 h, up to 95 mg/24 h; or from greater than 79.8 mg/24 h, from greater than 93.10 mg/24 h, from greater than 106.4 mg/24 h, up to 119.7 mg/24 h.

Said oxybutynin/rivastigmine combination may also be administered in a single TTS containing the two active ingredients in admixture each other in the same TTS or separated in the same patch in two different TTSs each delivering the aforementioned oxybutynin and rivastigmine daily doses.

According to an embodiment, the present invention provides a method for treating a patient suffering from an Alzheimer type dementia, which comprises daily administering to said patient a transdermal therapeutic system comprising oxybutynin, or a pharmaceutically acceptable salt thereof, in combination with a cholinesterase inhibitor selected from the group consisting of rivastigmine and pharmaceutically acceptable salts thereof, in which the amount of rivastigmine, is from 14.1 mg to 53.2 mg.

The invention also provides an oxybutynin TTS consisting of a patch system daily releasing from 3.9 mg to 7.8 mg per day, in particular from 3.9 mg/24 h to 5.8 mg/24 h, especially 3.9 mg/24 h, of oxybutynin for use for the treatment of an hypocholinergic disorder such as Alzheimer type dementia, in combination with a rivastigmine daily dose of from 14.1 mg to 53.2 mg.

The oxybutynin TTS for use according to the present invention may be in any oxybutynin delivering transdermal pharmaceutical form, such as a patch, a gel, a cream, a spray, an ointment, a lotion or a paste, wherein oxybutynin is present in admixture with the common diluents and permeation enhancers, said pharmaceutical form containing oxybutynin base or a pharmaceutically acceptable salt thereof, such as its hydrochloride, hydrobromide, sulfate, phosphate, mesilate, acetate, maleate, succinate, lactate, citrate, hydrogen tartrate, tartrate, napsilate or embonate.

The permeation enhancer may be any compound that allows the improved permeation of drugs through the skin (see for example the review in Pharmaceutical Technology, November 1997, pages 58-66, the disclosure of which is herein incorporated by reference in its entirety). Such substances may be lower ($C_1$-$C_4$) alkanols; fatty alcohols such as lauryl alcohol (dodecanol), alone or in combination with a lower alkanol; fatty acids such as linolenic acid or oleic acid; fatty acid esters such as isopropyl palmitate, stearate, linoleate, oleate or myristate; glycerol; glycerol monoesters such as glycerol monostearate, monolinoleate or monooleate; glycerol diesters; glycerol triesters such as triacetin; sucrose monostearate, monolinoleate or monooleate; sorbitan esters; fatty alcohol ethers having from 10 to 20 carbon atoms; glycols, such as diethylene glycol or propylene glycol; glycols lower alkyl ethers, such as diethylene glycol mono($C_2$-$C_4$)alkyl ether, in particular diethylene glycol monoethyl ether.

These permeation enhancers are present in an amount from 0.01 to 20% by weight of the total weight of the composition, advantageously in an amount of from 0.05 to 10% by weight, preferably from 0.1 to 5% by weight.

Advantageously, the oxybutynin TTS releases 3.9-5.85 mg/day of oxybutynin, administered in combination with a rivastigmine daily dose from 14.1 to 46 mg. The preferable combination is an oxybutynin patch delivering 3.9 mg/day of oxybutynin and an oral or transdermal rivastigmine daily dose of from 18.4 to 46 mg. A routine treatment can be made with a combination of an oxybutynin patch delivering 3.9 mg/day of oxybutynin and an oral or transdermal rivastigmine daily dose of from 18.4 mg to 46 mg/24 hours. In particular, a TTS consisting of a patch is obtained as described for example in U.S. Pat. Nos. 5,212,199, 5,227,169, 5,747,065, 6,743,441, 7,081,249, 7,081,250, 7,081,251, 7,081,252, 7,087,241, US 2004/0057985 U.S. Pat. No. 8,420,117, US 2014/0271796, U.S. Pat. Nos. 8,802,134, 8,877,235, the disclosures of which are each incorporated herein by reference in their entirety.

Typically, a TTS in form of a patch is manufactured by mixing a predetermined amount of oxybutynin, of rivastigmine or of an association of the two drugs with the aforementioned permeation enhancer in a laminated composite which basically contains at least one reservoir comprising a adhesive which is a pressure-sensitive adhesive suitable for the contact with the skin, a backing layer and a strip to be removed just before the application of the patch on the subject's skin. The oxybutynin TTS may be manufactured according to one of the methods illustrated in the above-cited patent documents.

A TTS consisting of non-occlusive topical formulation for transdermal administration of oxybutynin is obtained as described for example in EP 0966972, U.S. Pat. Nos. 4,889,845, 6,962,691, US 2003/0170194, US 2005/0064037, US 2006/0147383, U.S. Pat. Nos. 7,029,694, 7,179,483, US 2009/0018190, U.S. Pat. No. 8,241,662, US 2007/.0225379, US 2010/216880, U.S. Pat. Nos. 8,652,491, 7,425,340, 7,214,381, 7,470,433, US 2008/0260842, US 2014/0037713, the disclosures of which are each incorporated herein by reference in their entirety.

Typically, a TTS in form of a solution, cream, lotion, spray, ointment, gel, is manufactured by mixing a predetermined amount of oxybutynin or of a pharmaceutically acceptable salt thereof; of rivastigmine or of a pharmaceutically acceptable salt thereof; or of an association of the two drugs, with common pharmaceutically acceptable carriers or vehicles and, optionally, with a permeation enhancer, of a gelling agent or thickening agent.

In one embodiment, a water-based gel formulation comprises 0.5-5% (w/w) of a pharmaceutically acceptable oxybutynin salt; 10-80% (w/w) of a lower ($C_2$-$C_4$) alkanol; and 0.2-2.0% of thickening agent and a basic pH regulator. The preferred short chain alcohols are ethanol and isopropanol. The preferred gelling/thickening agents include cross-linked polymer of acrylic acid with a high molecular weight, for example cross-linked copolymer of acrylic acid and ($C_{10}$-$C_{30}$)-alkyl acrylate, carboxymethylcellulose, hydroxypropylcellulose. In addition, In addition, the gel formulation comprises the permeation enhancers at from 0.01% to 20% by weight of the total weight of the composition, advantageously from 0.05% to 10% by weight, preferably from 0.1% to 5% by weight. Preferred permeation enhancer is glycerol or a monoester, diester or triester thereof, such as triacetin.

In another embodiment, a water-based gel formulation comprises 0.5-5% (w/w) of oxybutynin base; 10-80% (w/w) of a lower ($C_2$-$C_4$) alkanol; and 0.2-2.0% of a thickening agent. In addition, the gel formulation comprises the permeation enhancers at from 0.01% to 20% by weight of the total weight of the composition, advantageously from 0.05% to 10% by weight, preferably from 0.1% to 5% by weight. The suitable permeation enhancers are those listed above, preferably being propylene glycol, mono ($C_1$-$C_4$)-alkylated diethylene glycol, propylene glycol laurate, isopropyl myristate, and methyl lactate.

In another embodiment, a TTS in form of a sprayable composition comprising oxybutynin or a pharmaceutically acceptable salt thereof in an aqueous or non-aqueous solution. Typically, a non-aqueous sprayable composition is an alcoholic solution in at least one ($C_2$-$C_4$)alkanol, containing oxybutynin or a pharmaceutically acceptable salt thereof in an amount of 0.5%-5% w/w, in respect of the total weight of the composition, from 20% to 90% w/w of a volatile silicone consisting of a linear or cyclic permethyl(tetra-deca)siloxane, such as hexamethyldisiloxane, octamethyltrisiloxane, decamethyltetrasiloxane, octamethylcyclotetrasiloxane and decamethylcyclopentasiloxane, and 0% to 15% of a permeation enhancer as defined above. The preferred volatile silicones are hexamethyldisiloxane (for example the product provided by Dow Corning®, DC Fluid 0.65 cSt), optionally containing silicone gum (for example the product provided by Dow Corning®, DC Silmogen Carrier), and octamethyltrisiloxane.

The formulation is obtained by mixing the various compounds mentioned below until a homogeneous and clear solution is obtained and the solution can be sprayed by a mechanical sprayer which mechanically pumps the compositions from a container, preferably in a metered dose, by conventional mechanisms through a nozzle which can directed at the desired site of application. The amount of propellant gas is regulated in order to propel the exact amount of oxybutynin.

For oral administration, the AChEI, that is preferably selected from the group consisting of huperzine A, tacrine, for example as hydrochloride, donepezil hydrochloride, galantamine, as hydrobromide, and rivastigmine, as hydrogen tartrate, is formulated by mixing the active ingredient with conventional pharmaceutical acceptable carriers enabling said active ingredients to be formulated in tablets, pills, dragees, orally disintegrating tablets, capsules and the like.

Carriers for IR tablets include for example starches, cellulose and derivatives thereof; lubricants such as talc, stearic acid or magnesium stearate; diluents such as talc, powdered cellulose, lactose, starches such as maize or corn starch, mannitol, sorbitol; disaggregating agents such as microcrystalline cellulose or crospovidone; lubricant such as polyethylene glycol or magnesium stearate; ligands such as methylcellulose, sodium carboxymethylcellulose, alginic acid, alginates; sweeteners, such as sucrose, dextrose, mannitol, saccharin; or flavoring agents such as natural or synthetic oils.

Carriers for orally disintegrating tablets include for example lubricants, aggregating, sweetening, flavoring or disaggregating agents as well as agents improving the buccal mucosa absorption of components (a) and (b) such as sorbitol, mannitol, lactose and cellulose.

The sweeteners contained in the orally disintegrating tablets may be natural, optional reduced sugars such as sucrose, dextrose, xylitol, mannitol or sorbitol, or synthetic product such as sodium saccharine or aspartame.

The flavoring agents are pharmaceutically acceptable flavors and tastes of synthetic and natural oils, the latter extracted from plants, leaves, flowers, fruits and their combinations, such as cinnamon, peppermint, anise and citron leaves, bitter almond, citrus fruits, in particular orange and/or lemon, linden and grapefruit oils. Also chocolate, vanilla or eucalyptus flavor and essences of fruit, in particular apple, pear, peach, strawberry, cherry, apricot, orange, lemon and grapes may be advantageously used.

Carriers and vehicles for ER tablets or capsules include retardant materials such as is acrylic and methacrylic acid polymers and copolymers; cellulose derivatives such as hydroxypropylmethylcellulose, hydroxyethylcellulose, hydroxypropylethylcellulose, hydroxypropylcelluloses, methylcellulose, ethylcellulose, or sodium carboxymethylcellulose; gums; waxes; glycerides or aliphatic alcohols or a mixture thereof.

Advantageous ER administration formulations are in form of a transdermal patch manufactured according to known technologies, for administering rivastigmine base continuously and transdermally through a selected area of intact skin in a controlled manner for a prolonged period of time to induce high rivastigmine blood levels in a human subject, in particular to a patient suffering from a dementia of Alzheimer type, said subject or patient being treated with said rivastigmine.

Besides the aforementioned excipients and permeation enhancers, carriers and vehicles for transdermal formulations include retardant materials such as acrylic and methacrylic acid polymers and copolymers; cellulose derivatives such as hydroxypropylmethylcellulose, hydroxyethylcellulose, hydroxypropylethylcellulose, hydroxypropylcelluloses, methylcellulose, ethylcellulose, or sodium carboxymethylcellulose; gums; waxes; glycerides or aliphatic alcohols or a mixture thereof.

Rivastigmine may be also administered as a brand preparation, in particular by orally administering multiple EXELON® immediate-release 6 mg-capsules or by applying multiple EXELON® patches releasing 4.6 mg/24 hours, 9.5 mg/24 hours, or 13.3 mg/24 hours on the subject's skin, to daily release rivastigmine at a dose of from 14.1 to 53.2 mg or from 19.95 to 53.2 mg, normally from 14.1 mg to 46 mg.

Thus, according to the present invention, rivastigmine Component (b), as hydrogen tartrate, is orally administered, in combination with the above-illustrated oxybutynin TTS Component (a), at a daily dose of from 15 mg, preferably 18 mg, to 48 mg, or also from 18 mg to 84 mg. As set forth above, rivastigmine Component (b) may also be transdermally administered at a daily dose of from 14.1 mg to 46 mg.

According to a further embodiment, the invention provides a TTS capable of concurrently delivering both oxybutynin and rivastigmine, as described above.

Specifically, said TTS is a patch containing both oxybutynin base and rivastigmine base, in the same reservoir or matrix.

Said TTS may also be a patch divided in two parts, concurrently releasing the aforementioned rivastigmine amounts, in admixture with the common solvents, polymers or co-polymers and permeation enhancers.

Preferably, Component (a) is oxybutynin in a TTS delivering said oxybutynin at a dose of from 3.9 mg/24 h to 7.8 mg/24 h; and Component (b) is rivastigmine in the same TTS, delivering from 5.06 mg/24 h to 46 mg/24 h rivastigmine, from 10.45 mg/24 h to 95 mg/24 h, or from 14.63 mg/24 to 119.7 mg/24 h rivastigmine, said TTS being a transdermal patch.

Similarly, the non-occlusive transdermal therapeutic systems, in particular the gel formulations and the spray formulations contain oxybutynin or a pharmaceutically acceptable salt thereof, in association with rivastigmine or a pharmaceutically acceptable salt thereof; and release the aforementioned oxybutynin amounts associated with the aforementioned rivastigmine amounts, in admixture with the common solvents, carriers and permeation enhancers.

Huperzine A may be used as a commercial preparation, by orally administering multiple 0.05-0.2 mg immediate-release oral unit forms such as tablets or capsules, to administer said huperzine A at a daily dose of from 0.6 mg to 1.6 mg.

Donepezil hydrochloride may be also used as a brand preparation, for example by orally administering multiple ARICEPT® immediate-release 5 mg- or 10 mg-tablets or the 23-mg tablets. In particular, donepezil hydrochloride may be orally administered, in combination with the above-illustrated oxybutynin TTS, at a daily dose of from 15 mg to 100 mg or from 15 mg to 70 mg. Thus, according to an advantageous embodiment, in the combination of the present invention, Component (a) is a TTS delivering oxybutynin at a dose of from 3.9 mg/24 h to 7.8 mg/24 h, and Component (b) is donepezil hydrochloride, in an oral pharmaceutical composition comprising said donepezil hydrochloride, in an amount of from 15 mg to 60 mg. in admixture with a pharmaceutical carrier. According to a preferred embodiment, the above illustrated TTS Component (a) is a patch delivering 3.9 mg/24 h oxybutynin and the AChEI Component (b) is donepezil hydrochloride in a 23-mg oral formulation. The above described oxybutynin TTS may also be combined with two 23-mg ARICEPT® doses, thus for example, safely administering donepezil hydrochloride at a daily dose 4.6 times higher than the recommended 10 mg-dose.

In another example, the combination of a patch delivering 3.9 mg/24 h oxybutynin with two 23-mg ARICEPT® doses and one 10-mg ARICEPT® dose is also well tolerated, thus allowing the administration of 56 mg of donepezil hydrochloride.

Galantamine, as hydrobromide, may be also administered as a brand preparation, for example by orally administering RAZADYNE® immediate-release 8 mg- or 12 mg-tablets or RAZADYNE® ER 8 mg-, 16 mg- or 24 mg-capsules. In particular, galantamine hydrobromide may be orally administered, in combination with the above-illustrated oxybutynin TTS, at a daily dose of from 36 mg to 96 mg, normally at a daily dose or from 36 mg to 72 mg, preferably in an ER-form.

An advantageous TTS-oxybutynin/huperzine A combination essentially consists of:
 (a) transdermal patch releasing from 3.9 mg/24 h to 7.8 mg/24 h oxybutynin; and
 (b) huperzine A, in an amount of from 0.3 mg to 2.0 mg in a pharmaceutical composition in dosage unit form, in admixture with a pharmaceutical carrier in an oral IR formulation.

A particularly advantageous TTS-oxybutynin/huperzine A combination essentially consists of:
 (a) transdermal patch releasing 3.9 mg/24 h oxybutynin; and
 (b) huperzine A, in an amount of from 0.3 mg to 0.8 mg in a pharmaceutical composition in dosage unit form, in admixture with a pharmaceutical carrier in an oral IR formulation.

An advantageous TTS-oxybutynin/donepezil hydrochloride combination essentially consists of:
 (a) transdermal patch releasing from 3.9 mg/24 h to 7.8 mg/24 h oxybutynin; and
 (b) donepezil hydrochloride, in an amount of from 23 mg to 92 mg in a pharmaceutical composition in dosage unit form, in admixture with a pharmaceutical carrier in an oral IR formulation.

Another advantageous TTS-oxybutynin/donepezil hydrochloride combination essentially consists of:
 (a) transdermal patch releasing from 3.9 mg/24 h to 7.8 mg/24 h oxybutynin; and
 (b) donepezil hydrochloride, in an amount of from 25 mg to 92 mg in a pharmaceutical composition in dosage unit form, in admixture with a pharmaceutical carrier in an oral IR formulation.

Another advantageous TTS-oxybutynin/donepezil hydrochloride combination essentially consists of:
 (a) transdermal patch releasing from 3.9 mg/24 h to 5.85 mg/24 h oxybutynin; and
 (b) donepezil hydrochloride, in an amount of from 23 mg to 70 mg in a pharmaceutical composition in dosage unit form, in admixture with a pharmaceutical carrier in an oral IR formulation.

Another advantageous TTS-oxybutynin/donepezil hydrochloride combination essentially consists of:
 (a) transdermal patch releasing from 3.9 mg/24 h to 7.8 mg/24 h oxybutynin; and
 (b) donepezil hydrochloride, in an amount of from 25 mg to 70 mg in a pharmaceutical composition in dosage unit form, in admixture with a pharmaceutical carrier in an oral IR formulation.

Another advantageous TTS-oxybutynin/donepezil hydrochloride combination essentially consists of:
 (a) transdermal patch releasing 3.9 mg/24 h oxybutynin; and
 (b) donepezil hydrochloride, in an amount of from 23 mg to 60 mg in a pharmaceutical composition in dosage unit form, in admixture with a pharmaceutical carrier in an oral IR formulation.

A particularly advantageous TTS-oxybutynin/donepezil hydrochloride combination essentially consists of:
 (a) transdermal patch releasing 3.9 mg/24 h oxybutynin; and
 (b) donepezil hydrochloride, in an amount of from 25 mg to 60 mg in a pharmaceutical composition in dosage unit form, in admixture with a pharmaceutical carrier in an oral IR formulation.

Another particularly advantageous TTS-oxybutynin/donepezil hydrochloride combination essentially consists of:
 (a) transdermal patch releasing 3.9 mg/24 h oxybutynin; and
 (b) donepezil hydrochloride, in an amount of from 23 mg to 40 mg in a pharmaceutical composition in dosage unit form, in admixture with a pharmaceutical carrier in an oral IR formulation.

Another advantageous TTS-oxybutynin/donepezil hydrochloride combination essentially consists of:
 (a) transdermal patch releasing 3.9 mg/24 h oxybutynin; and
 (b) donepezil hydrochloride, in an amount of from 15 mg to 40 mg in a pharmaceutical composition in dosage unit form, in admixture with a pharmaceutical carrier in an oral IR formulation.

An advantageous TTS-oxybutynin/galantamine hydrobromide combination essentially consists of:
 (a) transdermal patch releasing from 3.9 mg/24 h to 7.8 mg/24 h oxybutynin; and
 (b) galantamine hydrobromide, in an amount (in galantamine) of from 18 mg to 96 mg in a pharmaceutical composition in dosage unit form, in admixture with a pharmaceutical carrier in an oral IR or ER formulation.

Another advantageous TTS-oxybutynin/galantamine hydrobromide combination essentially consists of:
 (a) transdermal patch releasing from 3.9 mg/24 h to 7.8 mg/24 h oxybutynin; and
 (b) galantamine hydrobromide, in an amount (in galantamine) of from 18 mg to 48 mg, in a pharmaceutical composition in dosage unit form, in admixture with a pharmaceutical carrier in an oral IR formulation, said Component (b) being intended to be administered twice per day.

Another advantageous TTS-oxybutynin/galantamine hydrobromide combination essentially consists of:
 (a) transdermal patch releasing from 3.9 mg/24 h to 7.8 mg/24 h oxybutynin; and
 (b) galantamine hydrobromide, in an amount (in galantamine) of from 36 mg to 96 mg, in a pharmaceutical composition in dosage unit form, in admixture with a pharmaceutical carrier in an oral ER formulation said Component (b) being intended to be administered once per day.

A particularly advantageous TTS-oxybutynin/galantamine hydrobromide combination essentially consists of:
 (a) transdermal patch releasing 3.9 mg/24 h oxybutynin; and
 (b) galantamine hydrobromide, in an amount (in galantamine) of from 30 mg to 36 mg, in a pharmaceutical composition in dosage unit form, in admixture with a pharmaceutical carrier in an oral IR formulation, said Component (b) being intended to be administered twice per day.

Another particularly advantageous TTS -oxybutynin/galantamine hydrobromide combination essentially consists of:
 (a) transdermal patch releasing 3.9 mg/24 h oxybutynin; and
 (b) galantamine hydrobromide, in an amount (in galantamine) of from 18 mg to 48 mg, in a pharmaceutical composition in dosage unit form, in admixture with a pharmaceutical carrier in an oral ER formulation,
said Component (b) being intended to be administered once a day.

An advantageous TTS-oxybutynin/rivastigmine combination essentially consists of:
(a) transdermal patch releasing from 3.9 mg/24 h to 7.8 mg/24 h oxybutynin; and
(b) rivastigmine, as free base or as its hydrogen tartrate salt, in a single dose (in rivastigmine) of from 13.20 mg to 120 mg in a pharmaceutical composition in dosage unit form, in admixture with a pharmaceutical carrier or vehicle in an IR or ER formulation.

An advantageous TTS-oxybutynin/rivastigmine combination essentially consists of:
(a) transdermal patch releasing from 3.9 mg/24 h to 7.8 mg/24 h oxybutynin; and
(b) rivastigmine, as free base or as its hydrogen tartrate salt, in an amount (in rivastigmine) of from 13.20 mg to 96 mg in a pharmaceutical composition in dosage unit form, in admixture with a pharmaceutical carrier or vehicle in an IR formulation,
said Component (b) being intended to be administered twice per day.

Another advantageous TTS-oxybutynin/rivastigmine combination essentially consists of:
(a) transdermal patch releasing from 3.9 mg/24 h to 7.8 mg/24 h oxybutynin; and
(b) rivastigmine, as free base or as its hydrogen tartrate salt, in an amount (in rivastigmine) of from 13.20 mg to 84 mg in a pharmaceutical composition in dosage unit form, in admixture with a pharmaceutical carrier or vehicle in an oral IR formulation,
said Component (b) being intended to be administered twice per day.

Another advantageous TTS-oxybutynin/rivastigmine combination essentially consists of:
(a) transdermal patch releasing from 3.9 mg/24 h to 7.8 mg/24 h oxybutynin; and
(b) transdermal patch releasing from 5.06 mg/24 h to 46 mg/24 h rivastigmine.

A particularly advantageous TTS-oxybutynin/rivastigmine combination essentially consists of:
(a) transdermal patch releasing from 3.9 mg/24 h to 7.8 mg/24 h oxybutynin; and
(b) transdermal patch releasing from greater than 27.6 mg/24 h rivastigmine.

Another particularly advantageous TTS-oxybutynin/rivastigmine combination essentially consists of:
(a) transdermal patch releasing from 3.9 mg/24 h to 5.85 mg/24 h oxybutynin; and
(b) transdermal patch releasing from greater than 32.2 mg/24 h rivastigmine.

A preferred TTS-oxybutynin/rivastigmine combination essentially consists of:
(a) transdermal patch releasing 3.9 mg/24 h oxybutynin; and
(b) transdermal patch releasing from 10.45 mg/24 h to 95 mg/24 h rivastigmine.

Another preferred TTS-oxybutynin/rivastigmine combination essentially consists of:
(a) transdermal patch releasing 3.9 mg/24 h oxybutynin; and
(b) transdermal patch releasing from greater than 57 mg/24 h rivastigmine.

Another preferred TTS-oxybutynin/rivastigmine combination essentially consists of:
(a) transdermal patch releasing 3.9 mg/24 h oxybutynin; and
(b) transdermal patch releasing from greater than 66.5 mg/24 h rivastigmine.

A preferred TTS-oxybutynin/rivastigmine combination essentially consists of:
(a) transdermal patch releasing 3.9 mg/24 h oxybutynin; and
(b) transdermal patch releasing from 14.63 mg/24 h to 119.7 mg/24 h rivastigmine.

Another preferred TTS-oxybutynin/rivastigmine combination essentially consists of:
(a) transdermal patch releasing 3.9 mg/24 h oxybutynin; and
(b) transdermal patch releasing from greater than 79.8 mg/24 h rivastigmine.

Another preferred TTS-oxybutynin/rivastigmine combination essentially consists of:
(a) transdermal patch releasing 3.9 mg/24 h oxybutynin; and
(b) transdermal patch releasing from greater than 93.1 mg/24 h rivastigmine.

The following example shows the result obtained with an oxybutynin TTS, as patch, in combination with a high dose of an AChEI such as rivastigmine, in patch too. The fact that rivastigmine (and other AChEIs such as donepezil hydrochloride and galantamine, as hydrobromide) may be safely administered at high doses without both any cholinergic, peripheral dose-limiting adverse effect (due to the AChEI) and any dose-limiting central anticholinergic effect (due to the anticholinergic oxybutynin) renders the treatment of a patient suffering from a hypocholinergic disorder such as Alzheimer type dementia or dementias of other types highly predictable for an enhanced efficacy. This fact, due to the antithetic action of the anticholinergic agent oxybutynin and of the cholinergic agent AChEI, is exhaustively illustrated in the above Detailed Description, the surprising feature being the unexpected absence of central dose-limiting anticholinergic adverse effects noted with the administration of oxybutynin.

EXAMPLE

A preliminary Phase I test in 5 healthy volunteers initiated by administering one EXELON® patch releasing 4.6 mg rivastigmine/24 hours, and went up by administering one patch every two days, until the subjects reached intolerable side effects. Then, the same subjects received the same intolerable dose of rivastigmine plus one OXYTROL® patch releasing 3.9 mg/24 h oxybutynin, and further went up with the rivastigmine dose every 2 days, until they reached an intolerable dose. In this test, 2 subjects did not tolerate even the first (lowest) dose of rivastigmine patch (4.6 mg/24 hours). However, these subjects tolerated receiving the rivastigmine patch concurrently with the oxybutynin patch and furthermore were able to tolerate even higher doses of the rivastigmine patch (up to 9.5 mg/24 hours in one subject and up to 27.6 mg/24 hours in the other subject). The remaining subjects averagely tolerated about 3.4 times or more the number of rivastigmine patches tolerated with the rivastigmine patch alone. At no time during the administration of any dose of rivastigmine plus oxybutynin were any signs of dose-limiting CNS side effects reported or observed.

The invention claimed is:

1. A pharmaceutical combination comprising, as Components:
   (a) oxybutynin or a pharmaceutically acceptable salt thereof, in a transdermal therapeutic system (TTS); and
   (b) an acetylcholinesterase inhibitor (AChEI); wherein said AChEI is rivastigmine, in an amount, per single dose, of from 9 mg to 120 mg, in a patch releasing from 14.62 mg/24 h to 119.7 mg/24 h.

2. The combination of claim 1, wherein said patch delivers rivastigmine at a rate from greater than 79.8 mg/24 h to 119.7 mg/24 h.

3. A pharmaceutical combination comprising, as Components:
   (a) oxybutynin or a pharmaceutically acceptable salt thereof, in a transdermal therapeutic system (TTS); and
   (b) an acetylcholinesterase inhibitor (AChEI);
   wherein said Component (a) is oxybutynin in a TTS delivering said oxybutynin at a dose of from 3.9 mg/24 h to 7.8 mg/24 h; and Component (b) is rivastigmine in the same TTS, delivering from 14.63 mg to 119.7 mg rivastigmine, said TTS being a transdermal patch.

4. A pharmaceutical combination comprising, as Components:
   (a) oxybutynin or a pharmaceutically acceptable salt thereof, in a transdermal therapeutic system (TTS); and
   (b) an acetylcholinesterase inhibitor (AChEI);
   wherein said AChEI is rivastigmine and pharmaceutically acceptable salts thereof.

* * * * *